United States Patent [19]

Heathcock et al.

[11] Patent Number: 4,950,775
[45] Date of Patent: Aug. 21, 1990

[54] ANTIHYPERCHOLESTEROLEMIC COMPOUNDS AND SYNTHESIS THEREOF

[75] Inventors: Clayton H. Heathcock, Kensington, Calif.; Terry J. Rosen, Waukegan, Ill.

[73] Assignee: University of California, Alameda, Calif.

[21] Appl. No.: 786,839

[22] Filed: Oct. 11, 1985

[51] Int. Cl.$^5$ ............................. C07F 7/08; C07F 7/18
[52] U.S. Cl. ................................... 550/438; 549/292; 549/417; 560/86; 560/89
[58] Field of Search ................. 549/292, 417; 560/86, 560/89; 556/438

[56] References Cited

U.S. PATENT DOCUMENTS

| | | | |
|---|---|---|---|
| 4,231,938 | 11/1980 | Monaghan et al. | 260/343.5 |
| 4,282,155 | 8/1981 | Smith et al. | 260/343.5 |
| 4,293,496 | 10/1981 | Willard | 260/343.5 |
| 4,294,846 | 10/1981 | Albers-Schonberg et al. | 424/279 |
| 4,294,926 | 10/1981 | Monaghan et al. | 435/125 |
| 4,319,039 | 3/1982 | Albers-Schonberg | 560/256 |
| 4,322,563 | 3/1982 | Hoffman | 568/425 |
| 4,342,767 | 8/1982 | Albers-Schonberg et al. | 424/250 |
| 4,343,814 | 8/1982 | Gullo et al. | 424/279 |
| 4,351,844 | 9/1982 | Patchett et al. | 424/279 |
| 4,375,475 | 3/1983 | Willard et al. | 424/279 |
| 4,420,491 | 12/1983 | Albers-Schonberg et al. | 424/311 |
| 4,432,996 | 2/1984 | Gullo et al. | 424/311 |
| 4,440,927 | 4/1984 | Prugh et al. | 549/292 |
| 4,444,784 | 4/1984 | Hoffman et al. | 424/279 |
| 4,450,171 | 5/1984 | Hoffman et al. | 424/279 |
| 4,459,422 | 7/1984 | Willard et al. | 560/59 |
| 4,470,981 | 9/1984 | Hesse | 424/238 |
| 4,472,426 | 9/1984 | Hoffman et al. | 424/279 |
| 4,474,971 | 10/1984 | Wareing | 549/214 |

FOREIGN PATENT DOCUMENTS 0142146   5/1985   European Pat. Off. ............. 560/51

OTHER PUBLICATIONS

Falck, J. R., Yang, Y-L., *Tetrahedron Letters* 25 (33), pp. 3563-3566 (1984).
Girotra, N. N., Wendler, N. L., *Tetrahedron Letters* 24 (35), pp. 3687-3688 (1983).
Girotra, N. N., Wendler, N. L., *Tetrahedron Letters* 23 (52), pp. 5501-5504 (1982).
Grieco, P. A., Zelle, R. E., Lis, R., Finn, J., *J.Am.Chem.Soc.* 105, pp. 1403-1404 (1983).
Hirama, M., Uei, M., *J.Am.Chem.Soc.* 104, pp. 4251-4253 (1983).
Hsu, C-T., Wang, N-Y, Latimer, L-H, Sih, C. J., *J.Am.Chem.Soc.* 105, pp. 593-601 (1983).
Wang, N-Y, Hsu, C-T., Sih, C. J., *J.Am.Chem.Soc.* 103, pp. 6538-6539 (1981).
Yang, Y-L, Manna, S., Falck, J. R., *J.Am.Chem. Soc.* 106, pp. 3811-3814 (1984).

*Primary Examiner*—Paul F. Shaver
*Attorney, Agent, or Firm*—Majestic, Parsons Siebert & Hsue

[57] ABSTRACT

A method of preparing compactin and mevinolin, ketoacid, enone, and glutarate analogs thereof, and related compounds. The compounds are prepared in substantially enantiomerically pure form using a structurally convergent synthesis. Total syntheses of (+)-compactin, (+)-mevinolin and related compounds are provided. Novel compounds are identified, several of which show significant anti-hypercholesterolemic activity.

19 Claims, No Drawings

ANTIHYPERCHOLESTEROLEMIC COMPOUNDS AND SYNTHESIS THEREOF

"This invention was made with Government support under Grant No.: GM29815 with the National Institute of Health and the University of California. The Government has certain rights in this invention."

FIELD OF THE INVENTION

This invention relates generally to antihypercholesterolemic compounds, and in particular relates to a novel method of providing such compounds in substantially enantiomerically pure form using a structurally convergent synthesis. The invention additionally relates to new antihypercholesterolemic compounds, and method of using the same.

BACKGROUND OF THE INVENTION

Atherosclerosis is a condition in which abnormal amounts of lipids are deposited in certain arteries, resulting in intimal thickening. The condition manifests itself by circulatory occlusion, principally of the coronary, cerebral, and peripheral arteries. Ensuing complications can lead to coronary heart disease, cerebrovascular disease, and some forms of peripheral vascular disease. These conditions are the major causes of death in the United States.

It has long been known that there is a relationship between atherosclerosis and high levels of plasma particularly cholesterol. In fact, hypercholesterolemia is a primary risk factor for coronary heart disease. In humans more than one-half of total body cholesterol is derived from de novo synthesis. Drugs that can be used to reduce the quantity of cholesterol thus biosynthesized are of potential value in treating hypercholesterolemia, and may also have utility as prophylactic agents for general use against atherosclerosis and coronary heart disease.

It has been discovered fairly recently that compactin (Formula 1) and a related compound, mevinolin (Formula 2) display utility as inhibitors of the enzyme hydroxymethylglutaryl coenzyme A reductase ("HMG CoA reductase").

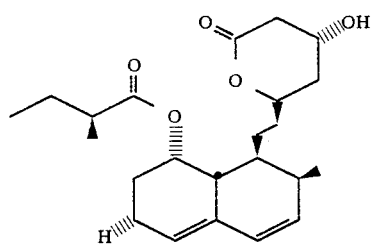

Formula 1

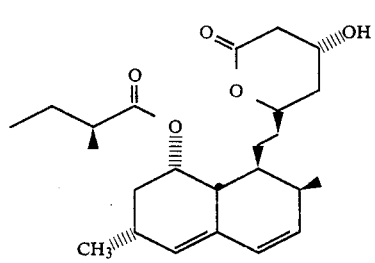

Formula 2

See, e.g., U.S. Pat. No. 4,049,495, U.S. Pat. No. 4,137,332, and U.S. Pat. No. 3,983,140, all issued to Endo et al. This class of natural products, distinguished by a highly functionalized hexalin or octalin unit and a β-hydroxy-δ-lactone portion linked by an ethylene bridge, are collectively referred to as mevinic acids. It has been demonstrated that the active form of these mevinic acids is the corresponding open-chain dihydroxy acid given by Formula 3 (as above, for compactin, "R" corresponds to -H; for mevinolin, to -CH₃).

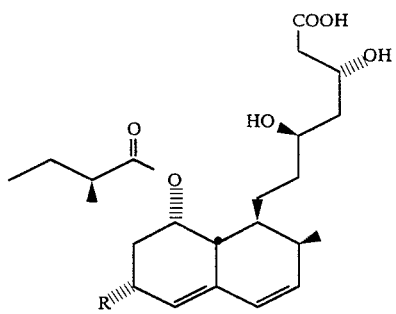

Formula 3 HMG CoA reductase catalyzes formation of mevalonate, a precursor in cholesterol biosynthesis, from HMG CoA, and is in fact the rate-controlling enzyme in the process. Thus, because compactin and mevinolin are potent as inhibitors of the biosynthesis of cholesterol, synthesis of these and related compounds is of some interest.

The first total synthesis of (+)-compactin was presented in 1981 by Wang et al. (Wang, N.-Y., Hsu, C.-T., and Sih, C.J., "Total Synthesis of (+)-Compactin," J. Am. Chem. Soc. 103, 6538 (1981); see also Hsu, C.-T., Wang, N.-Y., Latimer, L.H., and Sih, C.J., "Total Synthesis of the Hypercholesterolemic Agent Compactin," J. Am. Chem. Soc. 105, 593 (1983)), the key steps of which involve preparation of the enone shown in Formula 4, the cuprate of Formula 5, and admixture thereof.

Formula 4

Formula 5

Although in this way (+)-compactin is ultimately synthesized in approximately a 0.8% yield, the reaction sequence is a lengthy, complicated process involving harsh reaction conditions (thus necessitating protecting groups) and separation of stereoisomers at several intermediate points. A similar, "linear" synthesis of compactin has been presented by a different group and employs similar synthetic techniques (Girotra, N. et al., "A New Route in the Sequential Total Synthesis of Compactin," Tetrahedron Lett. 24, 3687 (1983)); however, similar problems have also been encountered.

Still another synthesis of (+)-compactin has been reported involving an intramolecular Diels-Alder reaction as the central synthetic maneuver (Hirama, M. et al., "Chiral Total Synthesis of Compactin," *J. Am. Chem. Soc.* 104, 4251 (1982)). A compound given by the structure shown in Formula 6 is synthesized by a Wadsworth-Emmons coupling, caused to cyclize, and then esterified.

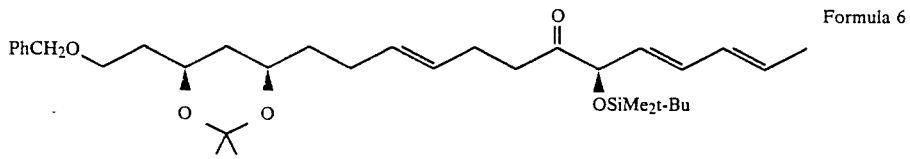

Formula 6

A similar method has been used to achieve synthesis of (+)-mevinolin. These syntheses share some of the difficulties encountered in the Wang et al. process outlined above, i.e. with regard to number of steps, use of harsh reagents, production of racemic mixtures rather than the enantiomerically pure compounds, etc. An additional problem encountered with the Hirama et al. syntheses is production of the desired stereoisomer as a minor product.

Several other syntheses appear in the patent literature. U.S. Pat. No. 4,440,927 to Prugh shows a method of synthesizing antihypercholesterolemic compounds such as compactin and mevinolin using a biphenyl-based compound (which becomes a substitute for the lower, "hexalin" portion of the molecule) and a chiral synthon (which becomes the lactone moiety). U.S. Pat. No. 4,474,971 to Wareing shows a method of making pyranone compounds, which, like compactin and mevinolin, are inhibitors of HMG CoA reductase. This latter method utilizes chemistry similar to that disclosed by Prugh for the upper portion of the molecule, although different protecting groups are employed; the process also involves use of a Wittig reagent. Problems with steric hindrance and other problems can easily arise with the Wittig reagents used.

The prior art methods of synthesizing compactin, mevinolin, and related compounds are for the most part lengthy, complicated syntheses which employ fairly harsh reagents and thus necessitate the use of protecting groups. A number of these prior methods also require separation of stereoisomers at intermediate points throughout the syntheses, further reducing the overall yield of the desired compounds and increasing the time as well as the number of synthetic steps involved. As may be seen, then, there is a need in the art for a total synthesis of compactin, mevinolin and related compounds which uses relatively few steps, mild reagents, and mild reaction conditions generally, which obviates the need for protecting groups, and ultimately provides the desired compounds in a high yield as well as in enantiomerically homogeneous form.

SUMMARY OF THE INVENTION

Accordingly, it is a primary object of the present invention to provide a structurally convergent method of synthesizing antihypercholesterolemic compounds.

It is another object of the present invention to provide a direct and efficient method of synthesizing compactin, mevinolin, and related compounds using relatively few steps, mild reagents, and mild reaction conditions, thus obviating the need for protecting groups throughout the synthesis.

It is yet another object of the present invention to provide a method of synthesizing compactin, mevinolin, and related compounds in a high yield and in enantiomerically pure form.

It is still another object of the present invention to provide novel compounds which are useful in the synthesis of compactin, mevinolin, and related ketoacid, enone, and glutarate structures, as well as other compounds.

It is a further object of the present invention to provide novel compounds which are inhibitors of HMG CoA reductase and are thus inhibitors of the biosynthesis of cholesterol.

It is still a further object of the present invention to provide a method of treating hypercholesterolemia.

Further objects and advantages will become apparent to those skilled in the art upon examination of the specification and the appended claims.

In one aspect of the present invention, a direct and efficient method of synthesizing antihypercholesterolemic compounds is provided. The method is a structurally convergent synthesis, and may be used to prepare such compounds as compactin, mevinolin, and related structures. The novel synthesis entails preparation of the lower, hexalin portion of the molecule, synthesis of a synthon for the upper, "C-1, C-6" moiety, and subsequent coupling of the two structures.

In another aspect of the present invention, novel compounds are provided by the above-outlined general method, which compounds are synthetically useful in a number of processes. At least several of these novel compounds show additional utility as inhibitors of cholesterol biosynthesis; in certain cases they are at least as effective in inhibiting HMG CoA reductase as compactin and mevinolin.

In a further aspect of the present invention, a method of treating hypercholesterolemia is provided which comprises administration of pharmaceutically acceptable salts of these biologically active novel compounds to hypercholesterolemic patients.

DETAILED DESCRIPTION OF THE INVENTION

Note on structural symbols unless otherwise indicated in the text accompanying the structures which follow, R indicates an alkyl substituent of less than about six carbon atoms, which is preferably either hydrogen or methyl; R' and R" are either hydrogen, alkyl, aryl, or arylalkyl, and are preferably either hydrogen, methyl, or phenylethyl; R* is hydrogen, alkyl, aryl, arylalkyl, or trialkylsilyl, and is preferably either hydrogen, methyl, benzyl, or t-butyldimethylsilyl; $R_1$ is hydrogen, alkyl, aryl, or arylalkyl, and is preferably phenyl or substituted phenyl; $R_2$ is hydrogen, alkyl, aryl, or arylalkyl, and is preferably an alkyl moiety of less than about eight carbon atoms, and still more preferably is 2-methyl; X and Y are either hydrogen, alkyl, OH, or OR*; Z is a hydrophobic moiety such as an alkyl chain, an ether functionality, or an acyloxy group, and is preferably S-2-methylbutyryloxy; X' is a halide substituent, and is preferably chloride or bromide; and A, B, C. and D indicate optional double bonds.

The process of this invention involves preparation of the compounds (+)-compactin and (+)-mevinolin, represented by Formulae 1 and 2, as well as structurally related compounds. The process is a convergent synthesis in which an aldehyde shown generally in Formula 7 is coupled with a synthon as shown in Formula 8.

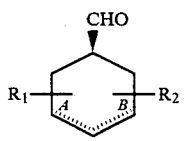

Formula 7

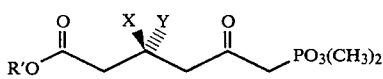

Formula 8

An enone compound having the general structure

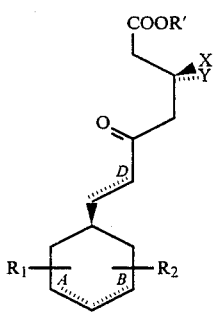

Formula 9 is thus initially provided; this enone analog has a double bond at the D position. Corresponding ketone (no double bond at D) and glutarate (see Formula 39) analogs may also be prepared. These three groups of structures will hereinafter sometimes be referred to as enone, ketone, and glutarate analogs, respectively. In Formulae 7 and 9, a douole bond may be present at either the A or B positions. A preferred aldehyde starting compound is the hexalin derivative

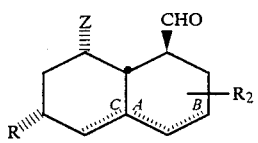

Formula 10 where a double bond may be present at the A, B, or C positions, or at both the B and C positions. A particularly preferred aldehyde starting compound is

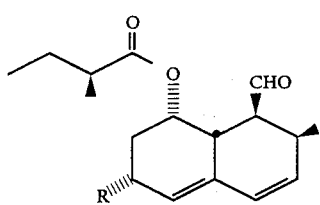

Formula 11 where R is either hydrogen or methyl, depending on whether a compactin (R=H) or a mevinolin (R=CH$_3$) analog is ultimately desired.

The enone structure of Formula 9 may, if desired, be reduced to provide the corresponding ketone compounds, i.e. structures having the double bond at D removed. Also, acid halide derivatives of Formula 8 may be used to prepare glutarate analogs, as will be discussed.

Synthesis of the hexalin structure will be described first, followed by a description of the lactone synthesis (i.e. synthesis of the "C-1, C-6" moiety). The complete synthetic process resulting in production of (+)-compactin and related compounds will then be outlined, and novel compounds synthesized in the development of the present method will be identified.

Experimental Methods: Unless otherwise noted, materials were obtained from commercial suppliers and used without further purification. Ether and tetrahydrofuran were distilled from sodium/benzophenone immediately prior to use. Hexamethylphosphoric triamide (HMPA) was distilled from calcium hydride and stored over 4 Å molecular sieves. Dichloromethane was distilled from phosphorus pentoxide. Boiling points and melting points are uncorrected. Infrared (IR) spectra were determined with a Perkin-Elmer Model 297 or Model 1420 infrared recording spectrophotometer. $^1$H NMR spectra were determined with the following spectrometers: Varian EM 390, UCB 200, or UCB 250 (super-conducting, FT instruments operating at 200 and 250 mHz, respectively). C NMR spectra were measured at 62.89 MHz with the UCB 250. All NMR spectra were determined with CDCl$_3$ as the solvent Chemical shifts are expressed in ppm downfield from internal tetramethylsilane. Significant $^1$ H NMR data are tabulated in order: multiplicity (s, singlet; d, doublet; t, triplet; q, quartet; m, multiplet), number of protons, coupling constants(s) in Hz. Mass spectra were obtained with Atlas MS-12, consolidated 12–110B or Kratos MS-50 mass spectrometers. Ultraviolet (UV) spectra were recorded with a Varian 219 UV spectrometer. Gravity column chromatography was done with Merck Silica Gel 60 (70–230 mesh ASTM), and flash chromatography was done with MN silica gel 60 (230–400 mesh ASTM). Thin layer chromatography (tlc) was performed with Analtech silica zation was effected with a 5% solution of 12-molybdophosphoric acid in ethanol or a solution of 10% vanillin and 5% sulfuric acid in 95% ethanol. High pressure liquid chromatography (hplc) was done with a Waters Model ALC/GPC-244 liquid chromatograph (analytical) or a Waters Prep LC/system 500 (preparative). μ-Porasil (manufactured by Waters Associates, Milford, Massachusetts; "Porasil" is a registered trademark of Waters Associates) columns were used unless otherwise indicated. Capillary glpc analysis was done with a Hewlett Packard 5790A series gas chromatograph (12 m, cross-linked methylsilicone, programmed, 45° C., 3° C./min). Elemental analyses were performed by the Microanalytical Laboratory, operated by the College of Chemistry, University of California, Berkeley, California.

Synthesis of the Hexalin Aldehyde

The present method involves preparation of a hexalin aldehyde such as that shown in Formula 11 in substantially enantiomerically homogeneous form from the corresponding mixture of diastereomeric alcohols shown in

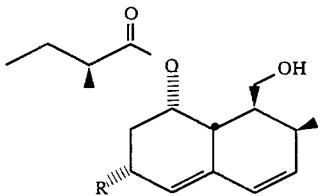

Formula 12

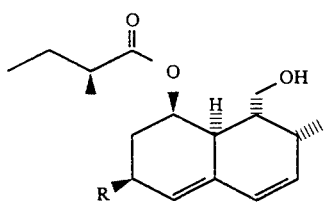

Formula 13

Although in principle the isomers are separable on the basis of their different physical properties, such as solubility and melting point, in practice it is convenient to convert them into esters of a carboxylic acid having an additional asymmetric carbon. Useful carboxylic acids for this purpose are the methyl ethers of (S)- or (R)-mandelic acid, preferably the former. The resulting mixture of diastereomeric diesters, shown in Formlae 14 and 15, are then separated by chromatography, preferably using silica gel as a solid phase. The separated isomer shown in Formula 14 is then subjected to selective hydrolysis of the ester function attached to the primary alcohol group. Potassium hydroxide in methanol is a particularly effective hydrolyzing agent.

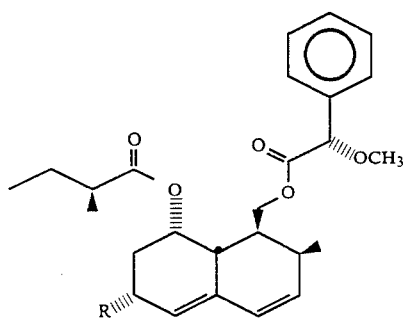

Formula 14

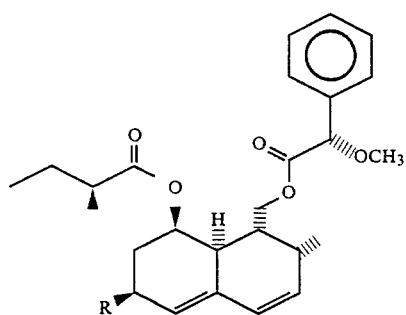

Formula 15

After removal of the 0-methylmandelyl group, the resulting hexalin alcohol (Formula 12), now substantially enantiomerically homogeneous, is treated with an oxidizing agent such as oxalyl chloride in dimethylsulfoxide at a temperature below about 0° C., preferably approximating −60° C. The resulting aldehyde is isolated, e.g., by extraction, and purified.

EXAMPLE 1

Preparation of (1SR, 2SR, 8SR, 8aRS)-2-Methyl8-[(S)-(2-methylbutyryl)oxy]-1[(S)-(O)- methylmandelyl-)oxymethyl]-1,2,6,7,8,8$a$hexahydronaphthalene (Formulae 14 and 15). Under a nitrogen atmosphere, into a 500 ml round-bottomed flask equipped with a rubber septum and a magnetic stirring bar were placed 690 mg (2.48 mmol) of a mixture of hexalin alcohols shown in Formulae 12 and 13, 31.7 mg (0.26 mmol) of 4-(N,N-dimethylamino)pyridine (DMAP), 436 mg (2.63 mmol) of (S)-0-methylmandelic acid and 4 ml of dichloromethane. To this stirring solution, at 0° C, was added 542 mg (2.63 mmol) of 1,3-dicyclohexylcarbodiimide. After stirring for 20 min at 0° .C and 12 h at room temperature, the reaction mixture was diluted with ether, and the white solids were removed by suction filtration. The filtrate was washed with 1 M aqueous $H_3PO_4$, saturated aqueous $NaHCO$ , and brine. The combined aqueous washings were extracted with ether, the combined organic fractions were dried ($MgSO_4$), and the solvent was removed with a rotary evaporator. The crude yellow oil was purified by column chromatography (20 g of silica gel) with 1:3 ether:hexanes as the eluant to obtain 996 mg (94% yield) of 0-methylmandelate esters. The diastereomers were separated by hplc (two $\mu$-Porasil semi-preparative columns and one semi-preparative column in series). IR (mixture, film): 3025, 2970, 1750, 1730, 1450 cm$^{-1}$. Isomer shown in Formula 14: H NMR: $\delta$0.68 (d, 3 J=6.8), 0.86 (t, 3, J =7.4), 1.10 (d, 3, J=7), 1.57 (m, 3), 2.03-2.45 (complex, 7), 3.41 (s, 3), 4.00 (t, 1, J=11), 4.19 (dd, 1, J=4, 11), 4.74 (s, 1), 4.99 (broad s, 1), 5.60 (m, 2), 5.94 (d, 1, J 9.6), 7.39 (m, 5). Isomer shown in Formula 15: $^1$H NMR: $\delta$0.72 (d, 3, J=6.8), 0.83 (t, 3, J =7.4), 1.06 (d, 3, J=7), 1.42 (m, 1), 1.62 (m, 2), 2.13 (m, 5), 2.36 (m, 2), 3.40 (s, 3), 3.96 (dd, 1, J=10, 11), 4.24 (dd, 1, J=3.8, 11), 4.74 (s, 1), 5.12 (broad s, 1), 5.56 (m, 2), 5.92 (d, 1, J=9.7), 7.38 (m, 5). Anal. (mixture of isomers) Calcd for $C_{26}H_{34}O_5$: C, 73.21; H, 8.03. Found: C, 73.18; H, 8.20.

EXAMPLE 2

Preparation of (1S,2S,8S,8aR)-1-Hydro- xymethyl-2-methyl-8-[(S)-(2-methylbutyryl)oxy]1,2,6,7,8,8$a$-hexahydronaphthalene (Formula 12). Under an argon atmosphere, into a 100 mL round-bottomed flask equipped with a rubber septum and magnetic stirring bar was placed 142 mg (0.33 mmol) of the diester shown in Formula 14. The system (cooled to 0° C.) was charged with 7.17 ml (0.66 mmol) of 0.092 M potassium hydroxide in methanol, and the solution was stirred for 5.5 h, during which time the ice bath melted and the cooling bath was maintained at 10 to 20° C. After warming to room temperature and stirring for a further period of 40 min, the reaction mixture was diluted with 70 ml of ether and washed with 10 ml of brine and 10 ml of water. The combined aqueous washings were extracted with 25 ml of ether, the combined organic fractions were dried over magnesium sulfate, and the solvent was removed with a rotary evaporator. The crude material (140 mg) was purified by column chromatography (6 g of silica gel) with 1:2 ether:hexanes as the eluant to obtain 92.4 mg (quantitative yield) of the hexalin alcohol shown in Formula 12 as a white crystalline solid. Material obtained in a similar manner was recrystallized from spectrophotometric grade pentane by slow evaporation at rom temperature to afford small white needles, mp 64.5-65.5° C., $[\alpha]_D^{25}$=+328° (c 0.42, CHCl$_3$). $^1$H NMR: δ0.89 (t, 3, J=7.4), 0.99 (d, 3, J=7.0), 1.14 (d, 3, J=7.0), 1.40–2.64 (complex, 11), 3.58 (t, 1, J=10), 3.79 (dd, 1, J=4.5, 10), 5.20 (m, 1), 5.58 (m, 1), 5.76 (dd, 1, J=5.4, 9.7), 5.99 (d, 1, J=9.7). Anal. Calcd for $C_{17}H_{26}O_3$: C, 73.34; H, 9.42. Found: C, 73.19; H, 9.26.

EXAMPLE 3

Preparation of (1R,2R,8R,8aS)-1-Formyl-2-methyl-8-[(S)-(2-methylbutyryl)-oxy]-1 2,6,7,8,8,a-hexahydronaphthalene (Formula 11; R=H). Under an argon atmosphere, in an oven-dried 10 ml round-bottomed flask were placed 24.0 mL (34.9 mg, 0.275 mmol) of freshly distilled (ClCO)2 and 0.58 ml of $CH_2Cl_2$. To this stirring solution, at −65° C., was added 0.14 ml (0.44 mmol) of a solution of 0.94 ml of DMSO in 4.0 ml of $CH_2Cl_2$. This solution was stirred at −65° C. for 2 min, and 49.6 mg (0.178 mmol) of the hexalin alcohol of Formula 12 was added to the system. The reaction mixture was stirred for 25 min at −60 to −70° C., and 0.15 ml (106 mg, 1.05 mmol) of $Et_3N$ was added to the system. The resulting white suspension was allowed to warm to room temperature, diluted with $CH_2Cl_2$, the combined organic fractions were dried over $MgSO_4$, and the solvent was removed with a rotary evaporator. The crude product was purified by column chromatographY (4 g of silica gel) with 1:1 ether:hexanes as the eluant to obtain 49.4 mg (quantitative yield) of hexalin aldehyde of Formula 11 as a white crystalline solid, mp 55–56° C. $^1$H NMR: δ0.87 (t, 3, J=7.4), 0.96 (d, 3, J=6.9), 1.08 (d, 3, J=7.0), 1.35–3.01 (complex, 10), 5.44 (m, 1), 5.67 (m, 1), 5.71 (dd, 1, J-4.1, 9.6), 6.00 (d, 1, J=9.7), 9.75 (d, 1, J=1.8). Anal. Calcd for $C_{17}H_{24}O_3$: C, 73.88; H, 8.75. Found: C, 74.02; H, 8.81.

Synthesis of the C-1, C-6 Moiety of Compactin and its Analogs

Scheme 1 illustrates preparation of the ketophosphonate synthon to be incorporated into the upper portion of compactin, or mevinolin, or related compound ultimately prepared.

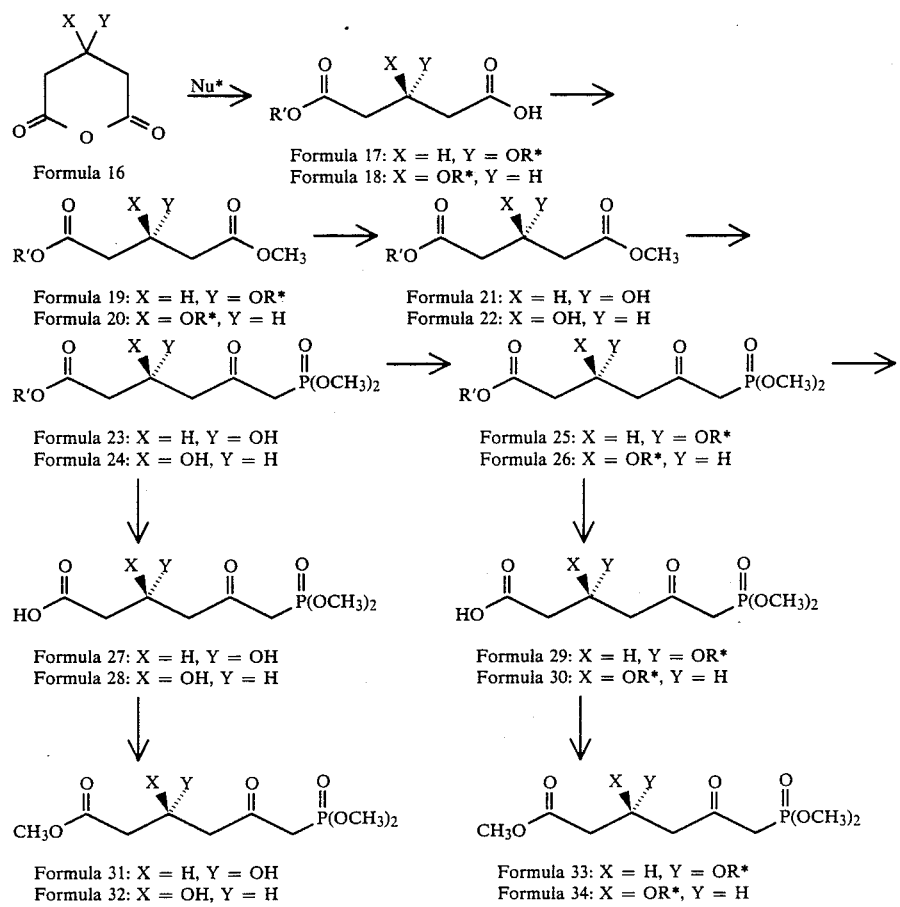

Scheme 1

R', X, Y, and OR* are as given earlier for the generalized etophosphonate synthon of Formula 8 (n.b.: X and Y may, in addition to the combinations illustrated, both be hydrogen). The anhydride shown in Formula 16 is thus converted to the synthons of Formulae 23 through 34, beginning with the opening of the initial ring structure with a nucleophile R'OH (designated Nu* in Scheme 1) which should be optically active in order to obtain optically active material after separation. An example of a preferred nucleophile is (R)-phenylethanol, shown in Formula 35.

The resulting open chain acid structure is then esterified with a suitable compound for this purpose; a preferred compound here is diazomethane, which will result in the methyl ester shown in Formula 19 or 20.

EXAMPLE 4

Preparation of (3R and 3S, 1′R)-Methyl (1′Phenylethyl) 3-(t-Butyldimethylsilyloxy) pentanedioate (Formula 19 and 20; $R^* = $t-Bu(CH$_3$)2Si, $R' = $(R)-1-phenylethyl). Under an argon atmosphere, into an ovendried 100 ml round-bottomed flask equipped with a magnetic stirring bar and a rubber septum were placed 6.63 g (54.3 mmol) of (R)-phenylethanol, 889 mg (7.29 mmol) of DMAP, 4.06 ml (2.94 g, 29.2 mmol) of Et$_3$N, and 15 ml of CH$_2$Cl$_2$. The system was cooled to $-60°$ C., and 7.12 g (29.2 mmol) of the anhydride of Formula 16 (X=H, Y=-OR*, R*=t-Bu(CH$_3$)$_2$Si,) was added. The resulting brown solution was warmed to $-40°$ C. over a period of 45 . The solution was and -15 to -20° C for 1.75 h. The reaction mixture was diluted with 150 ml of Et$_2$O and washed with 50 ml of 1 M aqueous H$_3$PO$_4$ and 20 ml of saturated aqueous NaHCO$_3$. The combined aqueous washings were acidified with 1 M aqueous H$_3$PO$_4$ and extracted with 50 ml of Et$_2$O. The combined organic fractions were dried over MgSO$_4$ and concentrated with a rotary evaporator to obtain 15.0 g of dark orange liquid which was used without further purification.

In a 500 ml round-bottomed flask (smooth glass joint) immersed in an ice bath was generated approximately 3.8 g (90 mmol, 0.3 M in ether) of diazomethane from Diazald (N-methyl-N-nitroso-p-toluenesulfonamide; "Diazald" is a registered trademark of the Aldrich Chemical Co., Milwaukee, Wisconsin). To this ice-cold solution was added the acid prepared above (Formulae 17 and 18) in a minimal amount of ether. The resulting solution was allowed to stand at room temperature for 1 h. Nitrogen was bubbled through the solution for 35 min (fire polished pipette), and this solution was allowed to stand over MgSO$_4$ overnight. Filtration followed by concentration with a rotary evaporator afforde d 14.0 g of orange liquid. The crude material was subjected to high vacuum for several hours, and the resulting liquid (13.0 g) was subjected to flash column chromatography (400 g of silica gel), eluting first with 1:6 ether:hexanes and then 1:5 ether:hexanes to obtain 7.13 g (69% yield) of an 8:1 mixture of the diesters of Formulae 19 and 20 as a colorless liquid. The diastereomers were separated by hplc. IR (CHCl$_3$):2970, 2870, 1750 cm$^{-1}$. Formula 19 (R′ =(R)-phenylethyl:- $[\alpha]_D^{25} = +21.9°$ (c, 2.03 CHCl$_3$). $^1$H NMR: δ0.00 (s, 3), 0.04 (s, 3), 0.80 (s, 9), 1.54 (d, 3 , J =6.6), 2.57 (m, 4), 3.66 (s, 3), 4.54 (m, 1), 5.88 (q, 1, J=6.6), 7.38 (m, 5). Formula 20: $^1$H NMR: δ0.05 (s, 6), 0.83 (s, 9), 1.54 (d, 3, J=6.6), 2.55 (m, 4), 3.65 (s, 3), 4.54 (m, 1), 5.88 (q, 1, J=6.6), 7.38 (m, 5). Anal. (mixture Calcd for C$_{20}$H$_{32}$O$_5$Si: C, 63.12; H, 8.48). Found: C, 63.66; H, 8.60.

The two diesters of Formulae 19 and 20 that are provided by the reaction of anhydride 16 with Nu* and subsequent esterification are then separated by chromatography, preferably by high performance liquid chromatography (hplc) using a suitable solid adsorbent phase larly effective); the 3R diastereomer shown in Formula 19 or the 3S diastereomer shown in Formula 20 is isolated and used in the steps which follow (if (R)-phenylethyl alcohol is used to effect the ring opening of anhydride 16, the compounds of Formulae 17 and 19 predominate; if (S)-phenylethyl alcohol is used to effect the ring opening, the compounds of Formulae 18 and 20 predominate). Either 19 or 20 may be then used in the preparation of antihypercholesterolemic agents. Removal of the protective group R* from the C-3 hydroxyl of 19 or 20 may be accomplished by treatment with hydrogen and a catalyst such as palladium, platinum, rhodium, or nickel if R* is benzyl. If the protective group R* is a trialkylsilyl group, such as t-butyldimethylsilyl, which is particularly effective for the purpose, deprotection may be carried out with a strong acid, such as sulfuric acid, p-toluenesulfonic acid, or hydrochloric acid, or with a source of fluoride ion such as tetra-n-butylammonium fluoride, potassium fluoride, or hydrofluoric acid; a preferred agent in this step is hydrofluoric acid.

EXAMPLE 5

Preparation of (3R, 1′R)-Methyl (1′-Phenylethyl) 3-Hydroxypentanedioate (Formula 21, R*=t-butyldimethyl-silyl; R′=(R)-1-phenylethyl). In an ovendried 100 ml round-bottomed flask equipped with a magnetic stirring bar was placed 1.00 g (2.63 mmol) of the 3R-isomer of the silyl ether of Formula 17. Twenty-five ml of a 1:19 solution of aqueous HF (Mallinckrodt, 40%) in CH$_3$CN was added to the system. The reaction mixture was stirred at room temperature for 75 min., diluted with 80 ml of ether, and washed carefully with two 15 ml portions of saturated aqueous NaHCO$_3$. The combined aqueous wash ings were extracted with 10 ml of ether, the combined organic fractions were dried over MgSO$_4$, and the solvent was removed with a rotary evaporator to afford 726 mg of pale yellow liquid. The crude product was purified by column chromatography (7 g of silica gel) with 2:1 ether:hexanes as the eluant to obtain 694 mg (99%) yield of the alcohol of Formula 21 as a colorless liquid. $^1$H NMR: δ1.55 (d, 3, J=6.6), 2.56 (m, 4), 3.36 (d, 1, J=4.0), 3.71 (s, 3), 4.47 (m, 1), 5.92 (q, 1, J=6.6), 7.38 (m, 5). Anal. Calcd for C$_{14}$H$_{18}$O$_5$: C, 63.14; H, 6.81. Found: C, 62.92; H, 6.87.

Application of the foregoing procedure with (S)-1-phenylethyl alcohol provides, in a similar manner, the alcohol of Formula 22 as a colorless liquid ($^1$H NMR data identical to that given for Formula 21).

The chiral ketophosphonate synthons shown in Formulae 23, 25, 27, 29, 31, and 33 are prepared fairly quickly and easily from the hydroxy ester of Formula 21. Similarly, the chiral ketophosphonate synthons shown in Formulae 24, 26, 28, 30, 32, and 34 are prepared from the hydroxy ester of Formula 22. It is these synthons which will be coupled in a Wadsworth-Emmons type reaction with the hexalin moiety of Formula 11.

The hydroxy ester of Formula 21 is, as shown, condensed with a dialkyl metallomethylphosphonate, preferably dimethyl lithiomethylphosphonate, to provide the ketophosphonate ester shown in Formula 23. The reaction is preferably conducted in an ethereal solvent such as diethyl ether, methyl t-butyl ether, or tetrahydrofuran (THF), at a temperature below about 0° C., and preferably approximating $-78°$ C. Preferred reaction time is from about 5 to about 30 minutes. Workup is carried out by acidifying the mixture with, e.g., hydrochloric, sulfuric, or phosphoric acid, after which ketophosphonate ester 23 is extracted (see Example 6). In an identical manner, the hydroxy ester of Formula 22 may be converted into the ketophosphonate of Formula 24.

As Scheme 1 illustrates, these ketophosphonate esters may be further reacted in one of two ways. First, the esters of Formulae 23 or 24 may be converted to the corresponding hydroxy acids of Formulae 27 or 28 by a catalyzed hydrogenolysis reaction. Suitable catalysts for the hydrogenolysis reaction include platinum, palladium, rhodium, and nickel; suitable solvents are preferably polar solvents and include diethylether, THF, ethylacetate, hexanes, acetate, and mixtures thereof. Hydrogen pressure may range anywhere from 1-100 atm, although the reaction does proceed at atmospheric pressure. Hydrogenolysis is carried out until a stoichiometric quantity of hydrogen is absorbed. The hydroxy acid structures thereby provided may then be further modified to yield additional ketophosphonate esters; esterification may be accomplished, for example, by treatment of the acid with diazomethane to give the methyl esters of Formulae 31 or 32.

Alternatively, the C-3 hydroxyl group of ketophosphonates of Formulae 23 and 24 may be protected. Suitable protecting groups include benzyloxymethyl or benzyl, which may be introduced by reaction of the alcohol with a benzyloxymethyl or benzyl halide and an amine such as diethylisopropylamine or triethylamine, and trialkylsilyl, which may be introduced by treatment of the alcohol with a silylating agent such as a trimethylsilyl halide or t-butyldimethylsilyl halide. A particularly preferred preferred protective group is t-butyldimethylsilyl, which may be conveniently introduced by treatment of the alcohol with t-butyldimethylsilyl chloride and an amine such as imidazole. If desired, the protected compound of Formulae 25 or 26 may be converted to the corresponding acids (Formulae 29 or 30) and thence to the methyl esters (Formulae 33 or 34) in a manner analogous to that described for the unprotected compounds.

EXAMPLE 6

Preparation of (S)-Dimethyl [4-Carbo[(R)phenylethoxy]-3-hydroxybutyryl]methylphosphonate (Formula 23; R'=R-phenylethyl). In an oven-dried 50 ml round-bottomed flask equipped with a magnetic stirring bar and a rubber septum was placed 11.9 ml (17.7 mmol) of 1.49 M n-BuLi in hexanes. The system was immersed in a room temperature water bath, and a stream of argon was passed over the solution to evaporate the hexanes. The system was immersed in a $-78°$ C. cooling bath and charged with 3.4 ml of THF. The cooling bath was removed until all of the n-BuLi was in solution. To this vigorously stirring solution, at $-78°$ C., was added 2.20 ml (2.52 g, 20.3 mmol) of dimethyl methylphosphonate over a period of 1 h, during which time 1 ml of THF was added. The resulting suspension was stirred at $-78°$ C. for 15 min. To the system was added dropwise a solution of 726 mg (2.73 mmol) of the hydroxy ester of Formula 21; R'=(R)-1phenylethyl), in 0.35 ml of THF. The syringe which delivered the ester was rinsed with 0.3 ml of THF. The reaction mixture was stirred at $-78°$ C. for 10 min., and an ice cold mixture of 13 ml of 1 M aqueous $H_3PO_4$ and ether was poured into the flask. After warming to room temperature, the mixture was partitioned between 1 M aqueous H PO and ethyl acetate. The layers were separated and the aqueous phase was extracted with ethyl acetate. The combined organic fractions were dried over $MgSO_4$, and the solvent was removed with a rotary evaporator to afford 1.11 g of light yellow liquid. The crude material was purified by flash column chromatography (8.5 g of silica gel), eluting first with ether and then with ethyl acetate to obtain 421 mg (43% yield) of phosphonate of Formula 23 (with R'=phenylethyl) as a pale yellow oil. IR ($CHCl_3$): 3570, 3010, 2870, 1720 cm$^{-1}$. $^1$H NMR: δ1.55 (d, 3, J=6.6), 2.56 (m, 2), 2.81 (m, 2), 3.12, 3.13 (2d, 2, J=23), 3.40 (d, 1, J=4.0), 3.78 (d, 6, J=11), 4.50 (m, 1), 5.91 (q, 1, J=6.6), 7.38 (m, 5). Anal. Calcd for $C_{16}H_{23}O_7P$: C, 53.63; H, 6.47. Found: C, 53.58; H, 6.59.

EXAMPLE 7

Preparation of (S)-Dimethyl [4-Carbomethoxy-3hydroxybutyryl]methylphosphonate (Formula 31). Into a 0 ml round-bottomed flask equipped with a magnetic stirring bar were placed 126 mg (0.35 mmol) of the ketophosphonate of Formula 23 (R'=(R)-1-phenylethyl), 7 ml of $Et_2O$, and 3 ml of EtOAc. To the system was added 83.3 mg of 10% Pd/C, and the flask was attached to an atmospheric hydrogenation apparatus. The system was placed under an atmosphere of $H_2$. The reaction mixture was stirred at room temperature for 1 h, diluted with EtOAc and filtered through a celite pad. The filtrate was concentrated with a rotary evaporator to obtain 80.1 mg of colorless oil.

In a 25 ml Erlenmeyer flask was placed 10 ml (2.4 mmol) of 0.24 M $CH_2N_2/Et_2O$. To this solution, at 0° C., was added the acid prepared above (see Formula 27) in a minimal amount of EtOAc. The cold bath was removed, and the solution was allowed to stand at room temperature for 15 min. $N_2$ was bubbled (fire-polished pipette) through the solution for 25 min. Concentration (rotary evap orator) afforded 91.0 mg of yellow oil which was purified by flash column chromatography (1 g of silica gel) with EtOAc as the eluant to obtain 63.0 mg (67% yield) of the methyl ester of Formula 31 as a colorless oil which was analytically pure. IR ($CHCl_3$): 2990, 1730 cm$^{-1}$. $^1$H NMR: δ2.54 (d, 2, J=6.3), 2.85 (m, 2), 3.15 (d, 1, J=23), 3.16 (d, 1, J=23), 3.43 (d, 1, J=4.1), 3.71 (s, 3), 3.80 (d, 6, J=11), 4.52 (m, 1). Anal. Calcd for $C_9H_{17}O_7P$: C, 40.30; H, 6.39. Found: C, 40.39; H, 6.43.

EXAMPLE 8

Preparation of (S)-Dimethyl [3-(t-Butyldimethylsilyloxy)-4-carbo [(R)-phenylethyloxy]butyryl]methylphosphonate (Formula 25; R*=t-butyldimethylsilyl; R'=R-phenylethyl). Under a nitrogen atmosphere, in a 10 ml round-bottomed flask were placed 226 mg (0.631 mmol) of the alcohol of Formula 23 and 0.6 ml of $CH_2Cl_2$. To this stirring solution were added 72.2 mg (1.06 mmol) of imidazole and 105 mg (0.70 mmol) of t-butylchorodimethylsilane. After stirring at room temperature for 3 h, 50 min., 24.0 mg (0.35 mmol) of imidazole and 35.0 mg (0.23 mmol) of t-butylchlorodimethylsilane were added to the system. After a further period of 2 h, 15 min., additional imidazole (8.0 mg, 0.12 mmol) and t- butylchlorodimethylsilane (12.0 mg, 0.080 mmol) were added. The reaction mixture was stirred for an additional period of 2 h, 5 min., diluted with EtOAc and washed with water. The organic phase was dried ($MgSO_4$) and concentrated with a rotary evaporator to afford 363 mg of light yellow oil. The crude material was purified by flash column chromatography (5 g of silica gel) with 2:1 EtOAc:hexanes as the eluant to obtain 251 mg (84% yield) of the silylated ketophosphonate of Formula 25 (R*, R'as given above) as a colorless oil. IR ($CHCl_3$): 3015, 2970, 2870, 1730 cm$^{-1}$ $^1$H NMR: δ0.02 (s, 3), 0.04 (s, 3), 0.81 (s, 9), 1.53 (d, 3, J=6.6), 2.48

(dd, 1, J=5.6, 15), 2.58 (dd, 1, J=6.0, 15), 2.87 (m, 2), 3.08 (d, 2, J=23), 3.77 (d, 6, J=14), 4.54 (m, 1), 5.87 (q, 1, J=6.6), 7.37 (m, 5). Anal. Calcd for $C_{22}H_{37}O_7SiP$: C, 55.91; H, 7.89. Found: C, 55.74; H, 7.95.

EXAMPLE 9

Preparation of (S)-Dimethyl [3-(t-Butyldimethylsilyloxy)-4-carbomethoxybutyryl]methylphosphonate (Formula 33; as in Example 8, R* is t-butyldimethylsilyl). In a 100 ml round-bottomed flask were placed 251 mg (0.53 mmol) of silylated ester 25 prepared in Example 8 (R* is t-butyldimethylsilyl) and 13 ml of $Et_2O$. To this solution was added 51.0 mg of 10% palladium on carbon, and the flask was attached to an atmospheric hydrogenation apparatus. The system was placed under an atmosphere of $H_2$. The reaction mixture was stirred at room temperature for 1 h, 55 min., diluted with EtOAc and filtered through a celite pad. The celite was rinsed well with EtOAc, and the filtrate was concentrated with a rotary evaporator to obtain 199 mg of a colorless oil which was used without further purification.

In a 100 ml round-bottomed flask were placed the crude acid prepared above (see Formula 29) and 1 ml of $Et_2O$. To this solution was cautiously added 7 ml (2.1 ml) of 0.3 M $CH_2N_2/Et_2O$ (prepared from Diazald), and the resulting so was allowed to stand at room temperature for 10-15 min. $N_2$ was bubbled through the solution (fire-polished pipette) until it was colorless. The reaction mixture was concentrated with a rotary evaporator, and the crude material (212 mg) was purified by flash column chromatography (3 g of silica gel) with 7:2 EtOAc:hexanes as the eluant to obtain 186 mg (92% yield) of the methyl ester of Formula 33 as a colorless oil. IR ($CHCl_3$) 2970, 2870, 1740 $cm^{-1}$. $^1H$ NMR: $\delta 0.06$ (s, 3), 0.07 (s, 3), 0.84 (s, 9), 2.46 (dd, 1, J=6.4 15), 2.56 (dd, 1, J=5.8, 15), 2.88 (d, 2, J=6.0), 3.11 (d, 2, J=23), 3.66 (s, 3), 3.790, 3.786 (2d, 6, J=11), 4.58 (m, 1), Anal. Calcd for $C_{15}H_{31}O_7PSi$: C, 47.10; H, 8.17. Found: C, 46.88; H, 8.27.

Scheme 2 illustrates preparation of an alternative, "C-1,C-5," synthon (in the form of the protected acyl halide of Formula 38) to be incorporated into the upper portion of the glutarate analogs of compactin, mevinolin, or related compound ultimately prepared. A general structure of such a glutarate analog prepared using the "C-1,C-5" synthon is shown in Formula 39; Formula 40 illustrates a particularly preferred embodiment thereof.

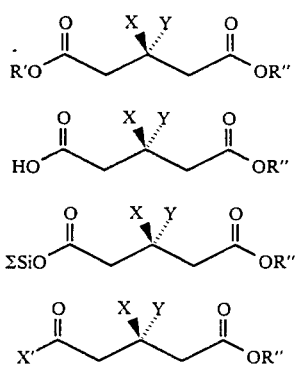

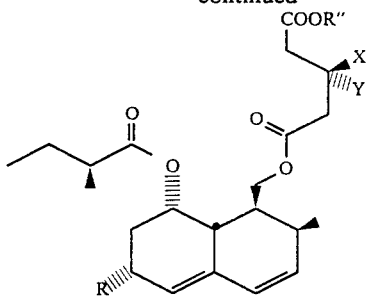

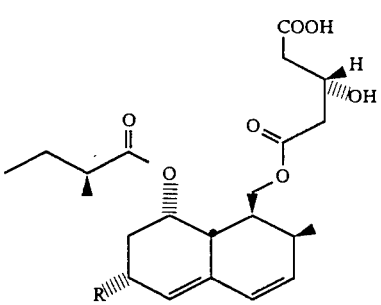

Scheme 2

R' R", R*, X, Y, and X' are as defined earlier ΣSi is trialkylsilyl, preferably t-butyldimethylsilyl. The diester shown in Formula 20 is treated with gaseous hydrogen in the presence of a catalyst such as palladium, platinum, rhodium, or nickel, preferably palladium deposited on carbon, whereupon the carboxylic acid of Formula 36 results. The reaction is carried out at a temperature of about $-30°$ C. to about $40°$ C., preferably about $25°$ C., in a compatible solvent such as ether, ethyl acetate, or hexane. Preferred reaction times range from about 10 minutes to about several hours; a particularly preferred reaction time is about three hours.

The carboxylic acid of Formula 36 is then converted to an activated derivative, preferably an acid chloride, in the manner which follows. The acid of Formula 36 is treated with an excess of a trialkylsilyl halide such as t-butyldimethylsilyl chloride to obtain a derivative of Formula 37. Treatment of the latter substance with a halogenating agent such as oxalyl chloride in the presence of N,N-dimethylformamide (DMF) at a temperature between about $-78°$ C. and about $30°$ C., preferably about $0°$ C., for a period between five minutes and four hours, preferably about two hours, in a suitable solvent provides the monoester mono acyl halide of Formula 38. Methylene chloride is a particularly preferred solvent for this reaction step. The proces is carried out with the diester of Formula 20 that has been puified by some method such as recrystallization or chromatography, and the resulting monoester monoacyl halide of Formula 38 is obtained in substantially enantiomierically pure form.

EXAMPLE 10

Preparation of monomethyl (R)-3-(t-butyldimethylsilyloxy)pentanedioate (Formula 36; X=OR*, Y=H, R*=t-butyldimethylsilyl, R'=(S)-1-phenylethyl, R"=CH ). In an oven-dried 100 ml round-bottomed flask was placed 74.2 mg (0.2 mmol) of diester of Formula 20 [R =t-butyldimethylsilyl, R'=(S)-1-phenylethyl)]and 4 ml of ether. To this solution was added 17.4 mg of 10% palladium on carbon (purchased from Englehard Industries). The flask was attached to an apparatus for maintaining an atmosphere of hydrogen. The mixture was stirred with a magnetic stirrer for 220 min and then filtered through pad of diatomaceous earth. Removal of solvent was accomplished with a rotary evaporator; 50.3 mg (93%) of acid of Formula 36 was obtained as a colorless oil. $^1$H NMR: δ2.59 (d, 2, J=6.4) 1 , 2.62 (d, 2, J=6.4), 3.73 (s, 3), 4.48 (quintet, 1, J=6.3).

EXAMPLE 11

Preparation of methyl t-butyldimethylsilyl (R)-3-(t-butyldimethylsilyl-oxy)pentanedioate (Formula 37; X=OR*, Y=H, R*=ΣSi=t-butyldimethylsilyl, R''=CH$_3$). In an oven-dried 10 ml round-bottomed flask was placed 53.9 mg (0.2 mmol) of the acid of Formula 36 prepared in Example 10, 0.25 ml of dichloromethane, 27.2 mg (0.4 mmol) of imidazole, and 30.1 mg (0.2 mmol) of t-butyldimethyl silyl chloride (purchased from Petrarch Chemical Company). The reaction mixture was stirred for 2 h at room temperature, diluted with 20 ml of ether, and then washed with 10 ml of water, 5 ml of saturated aqueous sodium bicarbonate, and 5 ml of brine. The combined aqueous washings were extracted with 10 ml of ether, which was added to the original organic solution. The combined organic solutions were dried over magnesium sulfate. After removal of the magnesium sulfate by filtration, the solvents were removed with a rotary evaporator to obtain 67.4 mg or the substance of Formula 37 as a colorless oil. The material may be purified by chromatography on silica gel to obtain a white crystalline solid, mp 44-46° C. IR (chloroform): 2950, 2860, 1735, 1720 cm$^{-1}$. $^1$H NMR: δ 0.06 (s, 3), 0.08 (s, 3), 0.26 (s, 6), 0.84 (s, 9), 0.93 (s, 9), 2.56 (m, 4), 3.67 (s, 3), 4.52 (quintet, 1, J=6.1). Anal. Calcd for $C_{18}H_{38}O_5Si_2$: C, 55.34; H, 9.80. Found: C, 55.50; H, 9.81.

EXAMPLE 12

Preparation of methyl (S)-3-(t-butyldimethyl roformylbutanoate (Formula 38; X=OR*, R*=t-butyldimethylsilyl, R''=CH$_3$, X'=Cl). In a 10 ml round-bottomed flask was placed 65.3 mg (0.167 mmol) of the bis-silyl derivative of Formula 37 prepared in Example 11 and 0.3 ml of a solution prepared from 2 drops of DMF in 3 ml of dichloromethane. To this solution, at 0° C., was added 24.4 mg (0.192 mmol) of oxalyl chloride, dropwise with a syringe. The resulting mixture was stirred for 1.5 h at 0° C. and for 40 min at room temperature. The volatile materials were removed with a rotary evaporator. The resulting acyl chloride is normally used directly, without further purification, for the formation of an appropriate ester, as will be discussed below.

Total Synthesis of (+)-Compactin and Related Compounds

The present process envisages a total synthesis of (+)-compactin and related compounds via a convergent method which couples the aldehyde structure represented by Formula 7 with one of the synthons prepared above. The reaction product is shown generally in Formula 9. In a preferred embodiment of the invention, the hexalin aldehyde shown in Formula 11 is coupled with one of the ketophosphonate synthons shown in Formulae 23-34. Again in Formula 11, R is alkyl, having less than about six carbon atoms, and is preferably either hydrogen or methyl, depending on whether a compactin or mevinolin analog is ultimately desired. The coupling is carried out using the known Wadsworth-Emmons process, and is illustrated by Scheme 3.

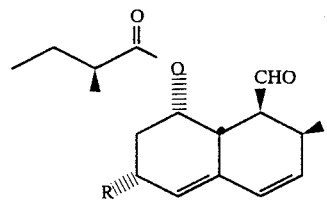

Formula 11

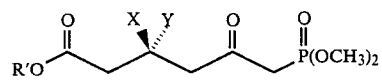

Formulae 23-34

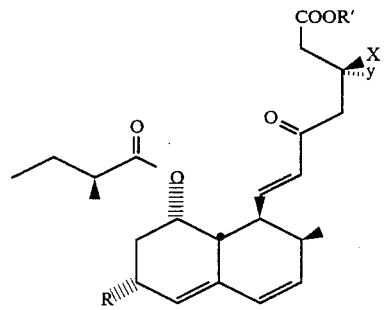

Formulae 41-52

Scheme 3

The X, Y, R* and R'substituents of the structures represented by Formulae 41 to 52 correspond to those of Formulae 23-34 above (see Table 1; not illustrated, however, is the alternative embodiment where X=Y=H). The hexalin aldehyde of Formula 11 is admixed with the selected synthon of Formulae 23-34 in a suitable polar solvent such as dimethylsulfoxide (DMSO), acetonitrile, or a mixture of tetrahydrofuran and N,N-dimethylformamide (DMF). An especially preferred solvent for this step is DMSO. A predetermined amount of an alkali metal halide salt such as LiCl is added to the solution, followed by an amount of an amine base such as triethylamine, diethylisopropylamine, or 1,8-diazabicyclo[5.4.0]undec-7-ene (DBU) at least equimolar to the amount of aldehyde present. The solution is stirred for at least about one hour at a temperature preferably ranging from about 0° C. to about 60° C., preferably about 25° C. The resulting enone compound is isolated and purified.

TABLE 1

| Formula No. | | | Preferred Substituents | | |
|---|---|---|---|---|---|
| Enone Analog | Ketone Analog | Glutarate Analog | X | Y | R', R'' |
| 41 | 53 | 59 | H | OH | * |
| 42 | — | 60 | OH | H | * |
| 43 | — | 61 | H | OR* | * |
| 44 | — | 62 | OR* | H | * |
| 45 | 54 | 63 | H | OH | H |
| 46 | — | 64 | OH | H | H |
| 47 | — | 65 | H | OR* | H |
| 48 | — | 66 | OR* | H | H |
| 49 | 55 | 67 | H | OH | CH$_3$ |
| 50 | — | 68 | OH | H | CH$_3$ |
| 51 | — | 69 | H | OR* | CH$_3$ |
| 52 | — | 70 | OR* | H | CH$_3$ |

*R', R'' as defined in text.
OR*As outlined in text.
R$_2$: 2-methyl.

EXAMPLE 13

Preparation of Compound 41 (R=H, R'=(R)-1phenylethyl, X=H, and Y=OH): Under an argon atmosphere, in an oven-dried 10 ml round-bottomed flask equipped with a magnetic stirring bar and a rubber septum were placed 7.9 mg (0.065 mmol) of hexalin aldehyde 11, 33.4 mg of ketophosphonate 23, and 50 ml of $CH_3CN$. To this stirring suspension was added about 20–30 g LiCl followed by 12.1 ml (12.3 mg, 0.081 mmol) of DBU. The mixture gradually became brown and homogeneous. The reaction mixture was partitioned between 6 ml of ether and 2 ml of $H_2O$. An additional 25 ml of ether was added, the layers were separated, and an ice-cold mixture of 8 ml of ether and 2 ml of 0.5 M aqueous $H_3PO_4$ was added to the organic phase. The layers were separated, and the organic phase was washed with brine. The ether solution was dried over $MgSO_4$ and concentrated using a rotary evaporator to afford 29.0 mg of pale yellow oil. The crude material was purified by column chromatography (2 g of silica gel) with 1:1 ether:hexanes as the eluant to obtain 14.0 mg (42% yield) of enone 41. IR ($CHCl_3$): 3420, 1730, 1670 cm$^{-1}$. $^1$H NMR: δ0.87 (t, 3, J=7.4), 0.99 (d, 3, J=7.0), 1.11 (d, 3, J=7.0), 1.29–2.89 (complex, 14), 1.55 (d, 3, J=6.6), 3.53 (d, 1, J=3.9), 4.49 (m, 1), 5.04 (broad s, 1), 5.62 (broad 2, 1), 5.72 (dd, 1, J=5.7, 9.8), 5.92 (q, 1, J=6.6), 6.02 (d, 1, J=9.4), 6.03 (d, 1, J=16), 6.83 (m, 1), 7.37 (m, 5). Anal. Calcd for $C_{32}H_{40}O_6$: C, 73.20; H, 7.93. Found: C, 72.95; H, 7.94.

EXAMPLE 14

Preparation of Compound 51 (R=H, R'=CH₃, X=H, Y=t-butyldimethylsilyloxy): Under an argon atmosphere, into an oven-dried 10 ml round-bottomed flask equipped with a magnetic stirring bar and a rubber septum were placed 22.1 mg (0.080 mmol) of aldehyde 11, 46.3 mg (0.121 mmol) of phosphonate 33, and 80 ml of DMSO. To the solution was added approximately 20 g LiCl. To this stirring suspension was added 12.0 ml (12.2 mg, 0.080 mmol) of DBU. The reaction mixture became dark orange, and all of the solids gradually dissolved. The reaction mixture was stirred at room temperature for 30 h and partitioned between ether and 4 ml of ice-cold 1 M aqueous $H_3PO_4$. The layers were separated, and the organic phase was washed twice with brine, dried over $MgSO_4$, and concentrated with a rotary evaporator to afford 61.2 mg of yellow oil. The crude product mixture was purified by column chromatography (6 g of silica gel; 1:5 Et₂0: hexanes - 2:5 Et₂0: hexanes - EtOAc) to obtain 23.6 mg (55% yield) of pure 51 as a colorless oil. IR 2940, 2865, 1760 cm$^{-1}$. $^1$H NMR: δ0.03 (s, 3), 0.05 (s, 3), 0.82 (s, 9), 0.86 (t, 3, J=7.4), 1.00 (d, 3, J=7.0), 1.10 (d, 3, J=7.0), 1.34–2.62 (complex, 12), 2.76 (m, 2), 3.65 (s, 3), 4.61 (m, 1), 4.99 (broad s, 1), 5.60 (broad s, 1), 5.71 (dd, 1, J=5.7, 9.7), 6.00 (d, 1, J=9.7), 6.03 (d, 1, J=16), 6.81 (m, 1). Anal. Calcd for $C_{20}H_{48}O_6Si$: C, 67.63; H, 9.08. Found: C, 67.72; H, 9.24.

The enones of Formulae 41–52 may then be reduced to give the corresponding ketone structures given by Formulae 53–55 (again, R'is either hydrogen, alkyl, aryl, or arylalkyl, as defined earlier; however, for purposes of the Examples, R'in structures 53–55 corresponds to phenylethyl, hydrogen, and methyl, respectively):

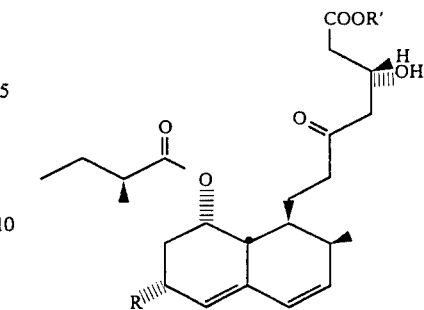

Formulae 53-55

This reduction may be accomplished by treatment of the selected enone of Formulae 41–52 with a silane derivative such as dimethylphenylsilane or triethylsilane, preferably triethylsilane, and a suitable transition metal catalyst, preferably tris(triphenylphosphine)rhodium(I) chloride. Preferred reaction temperatures range from about 25° C. to about 120° C., and a particularly preferred reaction temperature is about 70° C. The reaction mixture is concentrated and treated with an acid, base, or a source of flouride ion, a preferable reagent being hydrofluoric acid in acetonitrile. If the lower segment of the analog being synthesized does not contain olefinic or acetylenic bonds, the reduction may be accomplished more simply by the use of hydrogen gas and a heterogeneous catalyst such as palladium, platinum, rhodium, or nickel in a compatible solvent. Exemplary solvents include diethyl ether, hexanes, ethyl acetate, and methanol.

EXAMPLE 15

Preparation of hydroxy ketone 55 (R is H, R'is CH₃): Under an argon atmosphere, in a 10 ml round-bottomed flask equipped with a magnetic stirring bar and a rubber septum was placed 43.7 mg (0.082 mmol) of compound 51. To the system was added 0.8 ml of a solution of 5.0 mg of (Ph₃P)₃ClRh in 2.7 ml of benzene followed by 0.44 ml of triethylsilane. This stirring solution was heated at approximately 70° C. for 35 min. The reaction mixture was concentrated with a rotary evaporator and subjected to high vacuum for 5–10 min. To the flask containing the resulting orange oil was added 6 ml of a 1:19 mixture of 40% aqueous HF and $CH_3CN$. The reaction mixture was stirred at room temperature for 50 min., diluted with ether, and washed carefully with saturated aqueous $NaHCO_3$. The ether solution was dried ($MgSO_4$) and concentrated (rotary evaporator) to afford 43.6 mg of light yellow oil. The crude product was purified by column chromatography (2.5 g of silica gel) using 2:3 EtOAc:hexanes as the eluant to obtain 29.9 mg (87% yield) of hydroxyketone 28 as a colorless oil which became a waxy white solid upon standing in a refrigerator, mp 46-49° C. IR: 3540, 3480, 1760 cm$^{-1}$. $^1$H NMR: δ0.87 (t, 3, J=7.4), 0.87 (d, 3, J=7.0), 1.12 (d, 3, J=7.0), 1.33-2.67 (complex, 18), 3.39 (d, 1, J=3.7), 3.70 (s, 3), 4.45 (m, 1), 5.32 (broad s, 1), 5.56 (broad s, 1), 5.72 (dd, 1, J=6.0, 9.4), 5.97 (d, 1, J=9.7). HRMS: Calcd for $C_{24}H_{36}O_6$: 420.2511. Found: 420.2524.

The hydroxy ketones of Formulae 53–55 can then be reduced with a suitable reducing agent such as sodium borohydride, lithium aluminum hydride, zinc borohydride, lithium tri-t-butoxy aluminum hydride, or diisobutyl aluminum hydride, to give the diastereomeric diols shown in Formulae 56 and 57, which may then be easily separated. hydride. The reduction is carried out for a period of time ranging from about 1 minute to about several hours, preferably approximating 0.5 h; preferred temperature for the reaction range from about −78° C. to about 30° C., preferably approximating −15° C. Suitable solvents include THF, diethyl ether, isopropanol, ethanol, and methanol, and a particularly preferred solvent is methanol. Again, if the lower segment of the analog synthesized does not contain olefinic or acetylenic bonds, the reduction may be accomplished with hydrogen gas and a heterogeneous catalyst as above.

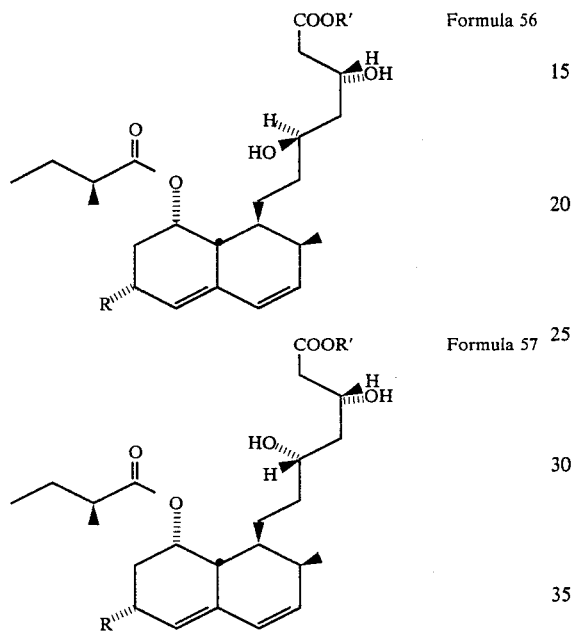

EXAMPLE 16

Preparation of diols 56 and 57 (R is H, R' is methyl): Under an argon atmosphere, into an oven-dried 10 ml round-bottomed flask equipped with a magnetic stirring bar and a rubber septum were placed 16.8 mg (0.040 mmol) of ketone 53 prepared in Example 16 and 0.8 ml of $CH_3OH$. To this stirring solution, at −14° C., was added 4.9 mg (0.13 mmol) of sodium borohydride. The reaction mixture was stirred at −13 to −15° C. for 27 min. To the system was added a mixture of 6 ml of ether and 3 ml of saturated aqueous sodium bicarbonate, the cold bath was removed, and the mixture was stirred at room temperature for 45 min. Additional ether was added, and the organic phase was separated from the aqueous phase and solids. The ether solution was washed with brine, dried ($MgSO_4$), and concentrated with a rotary evaporator to afford 19.0 mg of colorless oil. The crude product mixture was purified by hplc (μ-Porasil semi-preparative column, 2:3 EtOAc:hexanes, 4 ml min$^{-1}$ to obtain 9.6 mg of 56 and 4.6 mg of 57, each as a colorless oil.

Compound 56: $^1$H NMR δ0.88 (t, 3, j=7.4), 0.88 (d, 3, J=7.0), 1.11 (d, 3, j=7.0), 1.20–2.43 (complex, 16), 2.48 (d, 2, J=6.2), 3.41 (m, 1), 3.71 (s, 3), 3.81 (m, 2), 4.24 (m, 1), 5.35 (broad s, 1), 5.54 (broad s, 1), 5.73 (dd, 1, J=6.0, 9.6), 5.97 (d, 1, J=9.7).

Compound 57: IR: 3520, 1760 cm$^{-1}$. $^1$H NMR: δ0.89 (overlapping d and t, 6), 1.12 (d, 3, J=7.0), 1.222.58 (complex, 19), 3.44 (m, 1), 3.72 (s, 3), 3.88 (m, 1), 4.38 (m, 1), 5.34 (broad s, 1), 5.54 (broad s, 1), 5.74 (dd, 1, J - 6.1, 9.7), 5.97 (d, 1, J=9.7). HRMS: Calcd for $C_{24}H_{38}O_6$: 422.2668. Found: 422.2653.

Diol 56 may then be lactonized to give (+)compactin (Formula 1) as follows. The diol is treated with an acid such as hydrochloric, hydrofluoric, p-toluene sulfonic acid (p-TsOH) or with other strongly acidic substances in solvents such as methylene chloride, THF, diethyl ether, and toluene, at a temperature of between −30° C. and 40° C. for a period of time ranging from about 15 minutes to several hours. TsOH is an especially preferred acid for the lactonization, while benzene is a particularly preferred solvent; an especially preferred reaction temperature is about 25° C.

Correspondingly, diol 57 may be lactonized to give 5-epi-compactin (Formula 58).

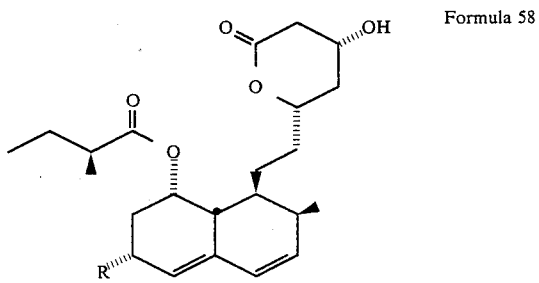

EXAMPLE 17

Preparation of (+)-compactin from diol 56 (R is H): Under an argon atmosphere, into an oven-dried 25 ml round-bottomed flask equipped with a magnetic stirring bar and a rubber septum were placed 9.6 mg (0.023 mmol) of 56 as prepared in Example 16 and 2.2 ml of benzene. To the system was added 2.2 mg (0.012 mmol) of p-TsOH.$H_2O$. The reaction mixture was stirred at room temperature for 40 min., concentrated (rotary evaporator), and 2.2 ml of fresh benzene was added. The mixture was stirred for 25 min. concentrated, and 2.2 ml of fresh benzene was added. The mixture was stirred for 10 min. and a small amount of solid $NaHCO_3$ was added. This mixture was stirred for 2 min., diluted with EtOAc, and washed with $H_2O$ and brine. The EtOAc solution was dried over $MgSO_4$ and concentrated with a rotary evaporator to afford 11.0 mg of crude product. This material was purified by column chromatography (1 g of silica gel) using 1:1 EtOAc:hexanes as the eluant to obtain 6.2 mg (70% yield) of 1. The $^1$H NMR spectrum of the material thus obtained was identical with that of a sample of the natural product. $^1$H NMR: δ0.89 (overlapping d and t, 6), 1.12 (d, 3, J=7.0), 1.23–2.20 (complex, 14), 2.35 (m, 3), 2.61 (ddd, 1, J=1.3, 3.8, 18), 2.74 (dd, 1, J=5.0, 18), 4.37 (broad s, 1), 4.62 (m, 1), 5.34 (broad s, 1), 5.56 (m, 1), 5.74 (dd, 1, J=6.0, 9.6), 5.98 (d, 1, J=9.7). HRMS: Calcd for $C_{23}H_{34}O_5$: 390.2406. Found: 390.2399.

EXAMPLE 18

Preparation of 5-epi-compactin from diol 57 (R is H): Under an argon atmosphere, in a 25 ml round-bottomed flask equipped with a magnetic stirring bar and a rubber septum were placed 4.6 mg (0.011 mmol) of diol 57 as prepared in Example 16 and 1.1 ml of benzene. To the system was added 1.1 mg (0.0057 mmol) of p-TsOH $H_2O$. The mixture was stirred at room temperature for 15 min. and approximately 1 mg of p-TsOH $H_2O$ was added to the system. After 20 min., the reaction mixture was concentrated with a rotary evaporator. To the system was added 1.1 ml of benzene. The reaction mixture was stirred at room temperature for 20 min., concentrated (rotary evaporator), and 1.1 ml of fresh benzene was added to the system. The mixture was stirred at room temperature for 20 min. and a small amount of solid $NaHCO_3$ was added to the system. After 2 min., this mixture was diluted with EtOAc and washed with water and brine. The organic solution was dried ($MgSO_4$) and concentrated with a rotary evaporator to afford 4.1 mg of oil. The crude product was purified by hplc using 1:1 EtOAc:hexanes as the eluant (4 ml min ) to obtain 3.3 mg of pure 5-epi-compactin 58. $^1$H NMR: δ0.89 (t, 3, J=7.4), 0.89 (d, 3, J=7.0), 1.12 (d, 3, J=7.0), 1.2-2.4 (couples, 17), 2.46 (dd, 1, J=8.0, 17), 2.90 (ddd, 1, J=1.3, 5.8, 17), 4.22 (m, 2), 5.31 (m, 1), 5.56 (m, 1), 5.73 (dd, 1, J - 5.8, 9.6), 5.98 (d, 1, J= 9.7). HRMS: Calcd for $C_{23}H_{34}O_5$: 390.2406. Found: 390.2401.

Preparation of the 5-keto analogs of compactin and mevinolin (Formulae 45 and 46, plus the additional analogous structure where X=Y=H) may, if desired, be carried out by appropriate selection of the C-1,C-6 synthon as outlined above, or it may be carried out as follows. Removal of the protective groups from the C-3 hydroxyl and the terminal carboxyl groups in the compounds of Formulae 41-53 provides 3R'hydroxy-5-keto carboxylic acids that are potent inhibitors of the enzyme 3-hydroxy-3-methylglutarylcoenzyme A reductase. The deprotection operations may be done in several different ways. For example, if the group R* is a trialkylsilyl group, such as t-butyldimethylsilyl, deprotection may be accomplished by treatment with a strong acid, such as sulfuric acid, p-toluenesulfonic acid, or hydrochloric acid, or a source of fluoride ion such as tetra-n-butylammonium fluoride, potassium fluoride, or hydrofluoric acid; a preferred method for removing the t-butyldimethylsilyl group is hydrofluoric acid. If R'is an alkyl group such as methyl, hydrolysis may be carried out without removal of the (S)-2-methylbutyryl moiety by treatment with a solution of an alkali metal hydroxide in a mixture of water and a cosolvent such as methanol, ethanol, or isopropyl alcohol; potassium hydroxide in aqueous methanol is especially convenient for this purpose.

EXAMPLE 19

Preparation of the hydroxy diester of Formula 49 (R =H, R'=$CH_3$, X =H and Y =OH). In an oven-dried 10 mL round-bottomed flask equipped with a magnetic stirring bar and a rubber septum was placed 9.6 mg (0.018 mmol) of the silyl ether of Formula 51 [R =H, R'=CH , R* =t-Bu($CH_3$)$_2$Si, X=H,Y=OR*]. To the system was added 0.18 mL of a 1:19 solution of HF in $CH_3CN$. The resulting solution was stirred at room temperature for approximately 1 h, diluted with ether, and washed carefully with two portions of saturated aqueous $NaHCO_3$. The ether solution was dried ($MgSO_4$) and concentrated with a rotary evaporator to afford 9.0 mg of colorless oil. The crude material was purified by column chromatography (1 g of silica gel) using 2:3 EtOAc/hexanes as the eluant to obtain 7.0 mg (93% yield) of pure hydroxy ester as a colorless oil. IR ($CHCl_3$): 3540, 2940, 1730, 1670 cm$^{-1}$. $^1$H NMR: δ0.90 (t, 3, J=7.4), 1.03 (d, 3, J =7.0), 1.14 (d, 3, J=7.0), 1.40 (m, 1), 1.62 (m, 2), 2.15 (m, 3), 2.32 (m, 2), 2.58 (m, 4), 2.74 (dd, 1, J=4.3, 17), 2.85 (dd, 1, J=7.8, 16), 3.59 (d, 1, J=4.0), 3.74 (s, 3), 4.50 (m, 1), 5.07 (broad s, 1), 5.65 (broad s, 1), 5.74 (dd, 1, J=5.6, 9.7), 6.04 (d, 1, J=9.7), 6.12 (d, 1, J=6.88 (m, 1). HRMS: Calcd for $C_{24}H_{34}O_6$: 418.2355. Found: 418.2340.

EXAMPLE 20

Preparation of the hydroxy acid of Formula 45. Under a nitrogen atmosphere, into a round-bottomed flask equipped with a magnetic stirring bar and a rubber septum was placed methyl ester of Formula 45. To the system was added 0.43 mL 90.043 mmol) of 0.1 M KOH in MeOH-$H_2O$ (2:1). The resulting yellow solution was stirred at room temperature for 85 min. To the system was added 5 mL of ether and 4 mL of saturated aqueous $NaHCO_3$. The layers were separated, and the ether solution was extracted with additional saturated aqueous $NaHCO_3$. Ethyl acetate was added to the combined bicarbonate extracts, and the mixture was acidified with 1 M aqueous $H_3PO_4$. The layers were separated and the aqueous phase was extracted with ethyl acetate. The combined EtOAc extracts were washed with brine, dried ($MgSO_4$), and concentrated with a rotary evaporator to obtain 7.2 mg of hydroxy acid as a colorless oil. IR ($CHCl_3$): 3550-2450, 1730, 1670, 1630 cm$^{-1}$. $^1$H NMR: δ0.88 (t, 3, J=7.4), 1.01 (d, 3, J=7.0),3 1.12 (d, 3, J=7.0), 1.41 (m, 2), 1.67 (m, 2), 2.10 (m, 3), 2.37 (m, 2), 2.60 (m, 4), 2.73 (dd, 1, J=3.9, 17), 2.86 (dd, 1, J=8.0, 16), 4.52 (m, 1), 5.06 (broad s, 1), 5.63 (broad s, 1), 5.72 (dd, 1, J=5.8, 9.7), 6.02 (d, 1, J=9.7), 6.05 (d, 1, J=16), 6.87 (dd, 1, J - 9.6, 16). HRMS: Calcd for $C_{23}H_{32}O_6$: 404.2199. Found: 404.2184.

EXAMPLE 21

Preparation of the hydroxy acid of Formula 53 (R'=H). Under a nitrogen atmosphere, in a 10 ml round-bottomed flask equipped with a rubber septum and a magnetic stirring bar was placed the keto ester of Formula 53 (R'=$CH_3$). To the system was added 0.18 ml 90.018 mmol) of 0.1 M KOH in MeOH-$H_2O$ (2:1). The resulting light yellow solution was stirred at room temperature for 95 min. The reaction mixture was partitioned between 5 ml of $Et_2O$ and 4 ml of saturated aqueous $NaHCO_3$ Additional ether was added, and the layers were separated. The ether solution was extracted with several portions of saturated aqueous $NaHCO_3$. To the combined bicarbonate extracts was added 10 ml of ether. The mixture was acidified with 1 M aqueous $H_3PO_4$, the layers were separated, and the aqueous phase was extracted with ether and ethyl acetate. The combined organic extracts were washed with brine, dried ($MgSO_4$), and concentrated with a rotary evaporator to obtain 2.7 mg of hydroxy acid as a colorless oil which was judged to be pure from its $^1$H NMR spectrum. $^1$H NMR: δ0.88 (t, 3, J=7.4), 0.88 (d, 3, J=7.0), 1.13 (d, 3, J=7.0), 1.2-2.5 (complex, 15), 2.56 (d, 2, J=6.2), 2.65 (m, 2), 4.46 (m, 1), 5.34 (broad s, 1) 5.56 (broad s, 1), 5.72 (dd, 1, J=6.0, 9.7), 5.98 (d, 1, J=9.7). MS (70 eV) m/z 406 (parent), 57 (base). Glutarate analogs shown generally by Formulae 59-70

Formulae 59-70

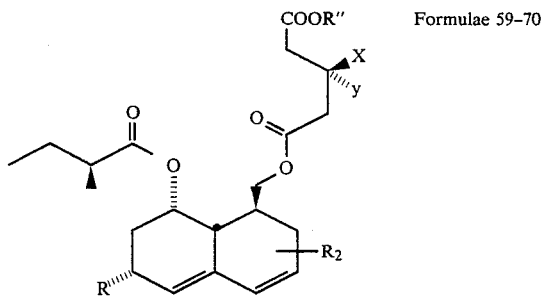

are prepared using the C-1,C-5 acid halide synthons described earlier. R", R₂ and R are as given earlier, and X and Y are either H, alkyl, or OR* (see Table 1 for particularly preferred substituents). The acyl halides of Formula 38 are useful synthons for coupling to suitable alcohols to prepare analogs of compactin and mevinolin that are effective inhibitors of the enzyme 3-hydroxy-3-methylcoenzyme A reductase. A particularly useful derivative of Formula 38 is the one in which R is t-Bu(CH₃)₂Si and X is Cl. This material may be coupled with the hexalin alcohol of Formula 12 to obtain a tri-ester of Formula 39. Selective cleavage of the terminal ester group may be accomplished by treatment of the triester with a solution of an alkali metal hydroxide in a mixture of water and an alcohol (or in a solvent mixture containing a hydroxylic component such as THF/water) or by treatment of the methyl ester of Formula 39 (R"=CH₃) with a strong nucleophile such as iodide or bromide in a dipolar aprotic solvent. A particularly effective method for accomplishing this selective cleavage is the use of lithium propylmercaptide in hexamethylphosphoric triamide (HMPA) at about 25° C. for a period of about 8 hours.

EXAMPLE 22

Preparation of (1S,2S,8S,8aR)-1-[(S)-(3-Hydroxy-4-carbomethoxybutyryl)-oxymethyl]-2-meth methyl-8-[(S)-(2-methylbutyryl)oxy]-1,2,6,7,8,8a hexahydronaphthalene (Formula 70; R=H, R'=CH , X=OR*, Y=H, R*=t-Bu(CH₃)₂Si) Under an argon atmosphere, in a 10 ml round-bottomed flask equipped with a magnetic stirring bar and a rubber septum were placed 0.47 mmol of the acid chloride of Formula 38 [R* =t-Bu(CH₃)₃Si, X=Cl]and 0.5 ml of dichloromethane. To this stirring solution, at 0° C., was added a solution of 0.039 ml (38.0 mg, 0.48 mmol) or pyridine in 0.2 ml of dichloromethane. To the system was added 26.0 mg (0.094 mmol) of alcohol 12. The reaction mixture was stirred for 8 h, during which time the ice bath gradually expired. The mixture was diluted with 30 ml of ether and washed with 1 M phosphoric acid, saturated aqueous sodium bicarbonate, and brine (5–10 ml portions). The combined aqueous washings were extracted with 20 ml of ether, the combined organic fractions were dried (magnesium sulfate), and the solvent was removed with a rotary evaporator to obtain 162 mg of yellow oil. The crude material was purified by column chromatography (8 g of silica gel) with 1:2 ether/hexanes as the eluant to obtain 53.3 mg of a silyl ether of Formula 70 [R* =t-Bu(CH₃)₂, R'=CH₃] as a colorless oil. IR (film): 2920, 2850, 1740 cm⁻¹. ¹H NMR: δ0.05 (s, 6), 0.83 (s, 9), 0.88 (complex, 6), 1.13 (d, 3, J=7.0), 1.45 (m, 1), 1.66 (m, 2), 2.15 (m, 4), 2.50 (complex, 7), 3.66 (s, 3), 3.96 (dd, 1, J=9.3, 11), 4.22 (dd, 1, J - 4.9, 11), 4.52 (m, 1), 5.15 (broad s, 1), 5.58 (broad s, 1), 5.72 (dd, 1, J=6.1, 9.5), 5.98 (d, 1, J=9.7).

Under a nitrogen atmosphere, in a 100 ml round-bottomed flask equipped with a magnetic stirring bar and a rubber septum was placed the foregoing silyl ether. To the system was added 4.0 ml of a 1:19 solution of 40% aqueous HF in CH₃CN. The resulting solution was stirred at room temperature for 1 h, 40 min, diluted with chloroform and washed with saturated aqueous sodium bicarbonate and brine. The combined aqueous washings were extracted with chloroform, the combined organic fractions were dried over magnesium sulfate, and the solvent was removed with a rotary evaporator to obtain 50.9 mg of light yellow oil. The crude material was purified by column chromatography (1.5 g of silica gel) with 3:2 ether/hexanes as the eluant to obtain 35.7 mg (85% yield from 12) of the compound of Formula 70 (R"=CH₃) as a colorless oil. IR (film): 3520, 2970, 1735 cm⁻¹. ¹H NMR: δ0.89 (t, 3, J=7.4), 0.93 (d, 3, J= 7.0), 1.13 (d, 3, J - 7.0), 1.42 (m, 1), 1.67 (m, 2), 2.18 (m, 4), 2.46 (complex, 7), 4.30 (d, 1, J=3.9), 3.71 (s, 3), 4.02 (dd, 1, J - 8.6, 11), 4.25 (dd, 1, J - 5.3, 11), 4.44 (m, 1), 5.18 (m, 1), 5.59 (broad s, 1), 5.71 (dd, 1, J -6, 9.6), 5.99 (d, 1, J=9.7). HRMS: Calcd for C₂₃H₃₄O₇: 422.2305. Found: 422.2306.

EXAMPLE 23

Preparation of (1S,2S,8S,8aR)-1-[(S)-(3- Hydroxy-4-carboxybutyryl)oxymethyl]-2-methyl-8-[(S)-(2methyl-butyryl)oxy]-1,2,6,7,8a-hexahydronaphthalene (Formula 40). To a solution of 31.1 mg (0.074 mmol) of methyl ester of Formula 34 [R"=CH₃]in 0.08 ml of oxygen- 0 free HMPA, at 0° C., was added 0.14 ml (0.077 mmol) of 0.56 M lithium propylmercaptide in oxygen-free HMPA. The mixture was stirred under a nitrogen atmosphere for 5 h, 40 min, during which time the ice bath melted. The brown solution was diluted with ether and washed with 1 M phosphoric acid and four portions (5–10 ml) of water. The ether solution was extracted with four portions of saturated aqueous sodium bicarbonate (40 ml). The bicarbonate extracts were acidified with 1 M phosphoric acid and extracted with four portions of chloroform (50 ml). The chloroform extracts were dried over magnesium sulfate, and the solvent was removed with a rotary evaporator to obtain 6.2 mg (20% yield) of acid of Formula 40 as a yellow oil. ¹H NMR: δ0.89 (t, 3, J=7.4), 9.30 (d, 3, J =7.0), 1.13 (d, 3, J=7.0), 1.2–2.65 (complex, 15), 4.03 (dd, 1, J=8.4, 11), 4.26 (dd, 1, J - 5.4, 11), 4.45 (m, 1), 5.19 (broad s, 1), 5.60 (broad s, 1), 5.71 (dd, 1, J=5.9, 9.6), 5.99 (d, 1, J=9.7).

New Compositions of Matter

In the process of developing the synthetic procedure outlined above, the inventors of the instant invention have synthesized a number of novel compounds. It is intended that these compounds as well as the above processes be considered within the scope of the appended claims.

For example, both the hexalin aldehyde of Formula 11 and the enantiomerically homogeneous hexalin alcohol of Formula 12 are novel. It is in part due to the availability of this latter compound in enantiomerically homogeneous form that novel syntheses are made possible.

Other novel compositions of matter to be considered within the scope of the instant inventions include the compounds described above and shown in Formulae 17-34, 41-55, 58, and 59-70. Pharmacologically acceptable salts of the carboxylic acid forms (R'=R"H) of the novel compounds are also considered to be within the scope of this invention; such compounds include the alkali metal salts of the compounds and in particular the sodium and potassium salts.

The essential steps of the synthesis of these compounds follow those outlined above, and are illustrated in Examples 22 and 23 above.

Method of Use of the Novel Compounds

Of the various compositions of matter identified as novel during the development of the instant synthetic process, all are extremely useful in a number of natural product syntheses, as illustrated above in the novel synthesis of (+)-compactin and related compounds. In addition, several of the enone, ketone, and glutarate erolemic agents, as they are also inhibitors of the enzyme HMG CoA reductase.

The antihypercholesterolemic activity of each novel compound was measured using the following test. The potency of compactin and each analog as an inhibitor of HMG CoA reductase catalysis was measured with rat liver microsomes. The liver preparation was stored at −78° C. Four concentrations of each compound ranging over four appropriate orders of magnitude were tested. The effect on the initial velocity of mevalonate production was determined in a radioactive assay system. Each 500-μL assay mixture contained 150 mM phosphate buffer, pH 6.8, 260 mM KCl, 16 mM Na$_2$EDTA, 7 mM dithiothreitol, 10.5 mM D- glucose-6-phosphate, 2.1 mM NADP, 20 M (R,S)-(3- C)-3- hydroxy-3-methylglutaryl coenzyme A, 2 units of D- o glucose-6-phosphate dehydrogenase and 240 μq of microsomal protein. All components but the $^{14}$C-HMG CoA were preincubated at 37° C. for 10 min. The inhibitor in 10 μL of DMSO was then added (control samples received DMSO only) and a 15-min. incubation was initiated by the addition of substrate. Catalysis was terminated with 33% aqueous KOH (50 μL). After 30 min., 25 μL of aqueous 0.05% bromophenol, 70000 dpm of (5-$^3$H)-mevalono-lactone in 25 μL of H$_2$O (recovery standard) and 90 μL of 5 N aqueous HCl were added. Samples sat for at least one hour, then were each passed through a column of Bio-Rad AG 1 ×8 exchange resin (200–400 mesh, formate form) and eluted with water. The sample volume plus 1.1 ml was allowed to elute before a 5-ml sample was collected for scintillation counting. Quantities of collected $^{14}$C-mevalonate mevalonate were corrected for $^3$-mevalonate recovery before conversion to catalytic rates. Each inhibitor concentration was assayed in triplicate and conversion of (S)-HMG Coenzyme A to product was always less than 20%. Rates in the presence of inhibitors were compared to control rates to generate % inhibition values. When % inhibition was plotted against inhibitor concentration, the resulting curve provided an IC$_{50}$ value for the inhibitor in question, IC$_{50}$ being defined as the concentration required to inhibit the enzyme by 50% of control. IC$_{50}$ values for compounds showing particularly significant antihypercholesterolemic activity are listed in Table 2.

TABLE 2

| Formula | IC$_{50}$, nM |
|---|---|
| 1 (compactin) | 9 |
| 53* | 16 |
| 41* | 230 |

TABLE 2-continued

| Formula | IC$_{50}$, nM |
|---|---|
| 63* | 300 |

*R' = R" = H, R' = H, X = H, Y = OH, R$_2$ = 2-methyl.

According to the above-outlined procedure, novel compounds within the scope of this invention possessing antihypercholesterolemic activity include the compounds given by Formulae 41, 53, 63 and reasonably equivalent isomers thereof. Accordingly, it is intended that the method of using these compounds in treating hypercholesterolemia, i.e. in inhibiting cholesterol biosynthesis by inhibiting the action of HMG CoA reductase, be considered within the scope of this invention as well. A reasonable dosage of compactin is known to range from about 15–100 mg/day; a particularly preferred dosage is about 30 mg/day. Corresponding dosages of the novel compounds synthesized herein are approximately proportional to the IC$_{50}$ values in Table 2 above.

While the various aspects of the inventive process and compounds have been described in conjunction with the preferred specific embodiments thereof, it is to be understood that all synthetic steps, reagents and reaction conditions reasonably equivalent to those described explicitly are also within the scope of this invention, as are all reasonably equivalent structures. The description given above is intended to be illustrative and not limitative of the various embodiments of this invention, the scope of which is defined by the appended claims.

We claim:

1. A structurally convergent process for synthesizing compactin, mevinolin and compounds related thereto in having a first moiety with the structure

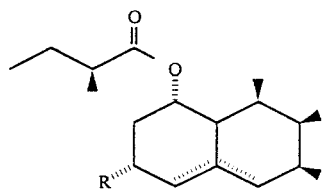

or having a second moiety with the structure

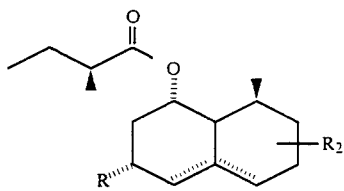

where R$_2$ is hydrogen or an alkyl of less than about 8 carbon atoms, comprising reacting an aldehyde having the structure

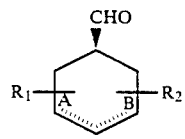

where $R_1$ and $R_2$ are hydrogen, alkyl, aryl or arylalkyl, with a ketophosphonate synthon having the structure

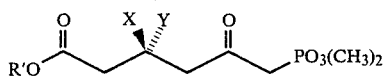

where R' is hydrogen, alkyl, aryl or arylalkyl, and X and Y are selected from the group consisting of hydrogen, alkyl, or -OR*, where R* is hydrogen, alkyl, aryl, arylalkyl, or trialkylsilyl, in a Wadsworth-Emmons coupling reaction.

2. The synthetic process of claim 1, whrein said reaction is carried out in a polar solvent in the presence of an amine base and an alkali metal halide salt at a predetermined temperature for a time sufficient to bring said reaction to substantial completion.

3. The synthetic process of claim 2, wherein said polar solvetn is selected from the group consisting of dimethylsulfoxide, acetonitrile, tetrahydrofuran, N,N-dimethylformamide, and mixtures thereof.

4. The synthetic process of claim 2, wherein said alkali metal halide salt is a lithium halide.

5. The synthetic process of claim 4, wherein said lithium halide is lithium chloride.

6. The synthetic process of claim 2, wherein said temperature is from about 0° C. to about 60° C.

7. The synthetic process of claim 6, wherein said temperature is about 25° C.

8. The synthetic process of claim 2, wherein said time sufficient for substantial completion is at least about one hour.

9. The synthetic process of claim 2, wherein said amine base is selected from the group consisting of 1,8-diazabicyclo[5.4.0]undec-7-ene, triethylamine, and diisopropylamine.

10. The synthetic process of claim 1, wherein said aldehyde is provided with a double bond at either the A or B positions.

11. The synthetic process of claim 10, wherein $R_1$ is a substituted or unsubstituted phenyl substituent.

12. The synthetic process of claim 11, wherein said aldehyde is a hexalin derivative having the structure

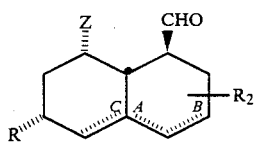

where R is hydrogen or an alkyl group having less than about six carbon atoms and Z is a hydrophobic moiety.

13. The synthetic process of claim 12, wherein R is hydrogen or methyl and Z is S-2-methylbutyryloxy.

14. The synthetic process of claim 13, wherein a double bond is present at the A, B or C positions, or at both the B and C positions.

15. The synthetic process of claim 14, wherein said hexalin aldehyde is prepared from the corresponding alcohol compound having the structure

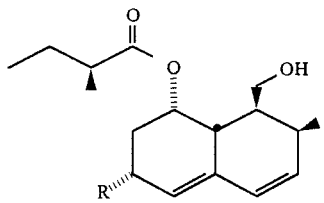

by treating said alcohol with an oxidizing agent.

16. The synthetic process of claim 1, wherein R' is selected from the group consisting of hydrogen, methyl, and phenylethyl, and R* is selected from the group consisting of hydrogen, methyl, benzyl, and t-butyldimethylsilyl.

17. The synthetic process of claim 16, wherein said ketophosphonate synthon is prepared by a process comprising:
opening a cyclic anhydride having the structure

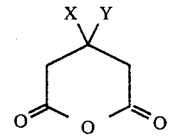

with an optically active nucleophile of formula R'OH, whereby corresponding open-chain carboxylic acid structures result;
esterifying said carboxylic acid structures;
preparing from said esterified compounds ketophosphonate synthons having the structure

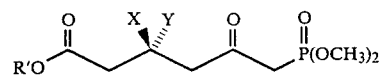

18. The synthetic procwess of claim 1, wherein said compounds synthesized by said Wadsworth-Emmons coupling are enones of the structure:

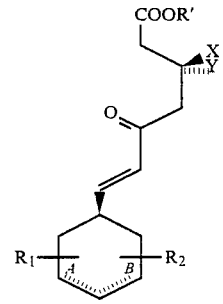

19. The synthetic process of claim 18, wherein sadi enones are further reduced to give the corresponding ketone derivatives having the structure

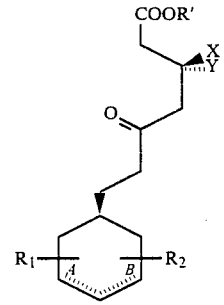

* * * * *

UNITED STATES PATENT AND TRADEMARK OFFICE
CERTIFICATE OF CORRECTION

PATENT NO. : 4,950,775

DATED : August 21, 1990

INVENTOR(S) : Clayton H. Heathcock

It is certified that error appears in the above-identified patent and that said Letters Patent is hereby corrected as shown below:

Column 30, line 36, in Claim 18:  replace "procwess" with --process--

Column 30, line 52, in Claim 19:  replace "sadi" with --said--

Signed and Sealed this

Seventh Day of January, 1992

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,950,775

DATED : August 21, 1990

INVENTOR(S) : Clayton H. Heathcock, Terry J. Rosen

It is certified that error appears in the above-identified patent and that said Letters Patent is hereby corrected as shown below:

Title Page of Patent: replace "[73] Assignee: University of California, Alameda, Calif."

with --[73] Assignee: The Regents of the University of California, Berkeley, Calif.--

Column 30, line 52, in Claim 19: replace "18" with --17--

Signed and Sealed this

Thirteenth Day of April, 1993

Attest:

STEPHEN G. KUNIN

Attesting Officer

Acting Commissioner of Patents and Trademarks